United States Patent [19]

Clarke et al.

[11] Patent Number: 5,750,591
[45] Date of Patent: May 12, 1998

[54] DENTURE ADHESIVE CONTAINING PARTIAL ZIRCONIUM, CALCIUM, SODIUM GANTREZ SALT

[75] Inventors: Hal C. Clarke, Elmont, N.Y.; Hyung-Kook Ahn, East Brunswick, N.J.; Eddie Wong, New Providence, N.J.; Robert C. Gasman, Montville, N.J.; Alfred J. Smetana, Wayne, N.J.; Joseph Synodis, Summit, N.J.; Tiang Shing Chang, Westfield, N.J.

[73] Assignee: The Block Drug Company, Jersey City, N.J.

[21] Appl. No.: 808,030

[22] Filed: Mar. 3, 1997

Related U.S. Application Data

[63] Continuation of Ser. No. 607,975, Feb. 29, 1996, abandoned.

[51] Int. Cl.$^6$ ............................. A61C 13/23; C08F 8/42
[52] U.S. Cl. .................... 523/120; 523/118; 524/45; 524/559; 525/370; 433/228.1
[58] Field of Search ....................... 523/120, 118; 524/559; 525/370

[56] References Cited

U.S. PATENT DOCUMENTS

| | | | |
|---|---|---|---|
| 3,003,988 | 10/1961 | Germann | 524/474 |
| 4,318,742 | 3/1982 | Lokken | 106/35 |
| 4,373,036 | 2/1983 | Chang et al. | 523/120 |
| 4,518,721 | 5/1985 | Dhabhar et al. | 523/120 |
| 4,521,551 | 6/1985 | Chang et al. | 523/120 |
| 4,569,955 | 2/1986 | Dhabhar | 523/120 |
| 4,758,630 | 7/1988 | Shah et al. | 525/207 |
| 4,910,247 | 3/1990 | Haldar et al. | 524/400 |
| 4,980,391 | 12/1990 | Kumar et al. | 524/45 |
| 5,001,170 | 3/1991 | Keegan | 523/120 |
| 5,006,571 | 4/1991 | Kumar et al. | 523/120 |
| 5,037,924 | 8/1991 | Tazi et al. | 526/272 |
| 5,073,604 | 12/1991 | Holeva et al. | 525/327.8 |
| 5,093,387 | 3/1992 | Schobel et al. | 523/120 |
| 5,147,941 | 9/1992 | Tazi et al. | 525/327.8 |
| 5,204,414 | 4/1993 | Pelah et al. | 525/328.9 |
| 5,298,534 | 3/1994 | Prosise et al. | 523/120 |
| 5,304,616 | 4/1994 | Rajaiah et al. | 526/240 |
| 5,369,145 | 11/1994 | Gasman et al. | 523/120 |
| 5,424,058 | 6/1995 | Rajaiah et al. | 523/120 |
| 5,525,652 | 6/1996 | Clarke et al. | 524/559 |

*Primary Examiner*—Tae Yoon
*Attorney, Agent, or Firm*—Craig M. Bell; Dann, Dorfman, Herrell & Skillman

[57] ABSTRACT

A denture adhesive with significantly improved hold performance is comprised of the mixed partial salts of polymethyl vinyl ether maleic acid. At least one of said salts comprises zirconium while a second salt is selected from the group consisting of calcium, zinc, magnesium, iron, strontium and mixtures thereof. Optionally, a tripartite salt formulation may be prepared utilizing sodium, lithium or potassium. The adhesives are formulated in a standard pharmaceutically acceptable vehicle comprised of waxes, oils, colorants, viscosity modifiers and the like as is known in the art. The denture adhesive may be formulated as a paste, powder or liquid which has rapid absorption characteristics for faster swelling softening and superior coalescence.

13 Claims, No Drawings

DENTURE ADHESIVE CONTAINING PARTIAL ZIRCONIUM, CALCIUM, SODIUM GANTREZ SALT

This is a continuation of application Ser. No. 08/607,975, filed Feb. 29, 1996 abandoned.

FIELD OF THE INVENTION

The present invention relates generally to denture adhesives for affixing dental prosthesis to oral tissues of the jaw and upper mouth regions in humans.

BACKGROUND OF THE INVENTION

A high quality denture adhesive should exhibit several desirable characteristics and functionalities. One such attribute is that it should quickly generate tacky, uniform and viscous mucilages upon contact with saliva so that the denture will be held in place as soon as it is seated in the mouth over the gums. It is also highly desirable that the mucilage possesses sufficient cohesive strength to withstand the stress of mastication and provides a cushion between the denture and its supporting gums or tissues during mastication. The denture fixative must also exhibit sufficient resistance to degradation under the environmental temperature and pH changes which occur in the oral cavity during such common actions as drinking hot beverages such as coffee or tea, cold beverages and highly acidic foods.

Traditionally, adherent paste and powders used to secure dentures within the mouth were prepared from such materials as finely powdered natural gums, i.e., karaya, acacia or tragacanth gum. These materials have the particular property of swelling to many times their original volume upon the addition of water to form a gelatinous or mucilaginous mass. Denture adhesive powders may be a combination of one or more natural gums, generally flavored with pleasant tasting volatile oils. Many other additives may also be included such as antiseptics, stabilizers, bactericides, special deodorants, plasticizing agents, fillers, coloring agents, and the like.

Paste forms of denture adherents, prepared from finely ground particles of the natural gums dispersed in a paste base, are also available and may be used instead of powder compositions. In any event, when wet with water, the natural gum in either the paste, powder or liquid formulation expands to become a viscous gel which acts as a cushion and as an adherent between the denture plate and the gum tissue.

Denture adhesive paste formulations have also been developed which are comprised mainly of natural or synthetic polymer materials suspended in an anhydrous oleaginous vehicle system comprising mineral oil and petrolatum. The petrolatum is added to thicken the formulation consistency to that of a paste which is extrudable from tubes. These formulations necessarily must be viscous to prevent syneresis or phase separation because the solid adhesive particles are merely suspended in the oily vehicle. High viscosity, on the other hand may also result in thick formulations which can make the paste somewhat difficult to squeeze out from the tube.

Historically, a denture adhesive paste is made by preparing a base and mixing the base with other components which will provide sufficient adhesion with adequate cohesive strength to hold the dentures in place. This adhesive paste must be non-toxic and non-irritating to oral tissues since they are in direct contact with the tissues and the dental prostheses. For a denture adhesive to be practical and provide comfort, it must not have an unpleasant odor and must have a pleasant taste and aroma. It also must exhibit adequate stability and quickly hydrate when in contact with the oral mucosa. It must also provide sufficient tack, develop high cohesive strength and it must be durable. In addition to all of the above, product appearance, taste and the ease of application of the product are also significant factors.

The dental adhesive composition must not only hydrate when contacted with oral fluids in order to form both a cushion and a cohesive seal with the oral tissues of the maxillary arch or inner surface of the mandibular arch, but it must also at the same time not be soluble when exposed to these same fluids such as saliva and the various foods and beverages that are exogenously introduced into the mouth.

Many efforts are constantly being made to develop improved denture fixative compositions. Both natural and synthetic hydrophilic polymers have been employed either singly or in combination in liquid, powder, paste or film formulations. U.S. Pat. No. 3,003,988 to Germann et al. describes a denture adhesive composition in which the denture fixative is a mixed partial salt containing calcium cation and alkali or quaternary ammonium cation of a lower alkyl vinyl ether-maleic anhydride type copolymer or its partial lower alkyl esters. Since then, many different denture compositions using this copolymer were disclosed as effective denture adhesives either in improved vehicles or in combination with other water soluble polymers or additives. See for example, U.S. Pat. No. U.S. Pat. No. 4,373,036 to Chang et al, U.S. Pat. No. 4,514,528 and U.S. Pat. No. 4,569,955 to Dhabhar et al., U.S. Pat. No. 4,910,247 to Haldar et al., U.S. Pat. No. 4,980,391 and U.S. Pat. No. 5,006,571 to Kumar et al., U.S. Pat. No. 5,037,924 to Tazi et al. and U.S. Pat. No. 5,093,387 to Schobel et al., all of which are hereby incorporated by reference.

U.S. Pat. No. 4,318,742 to Lokken discloses and claims a denture adhesive comprised of a major amount of gum base consisting of natural and synthetic gums, isobutylene/isoprene rubber, petrolatum waxes, polyethylene and mixtures thereof. The gum base is combined with a hydrophilic polymer such as methacrylic acid esters and carboxymethyl cellulose and the like to form the adhesive which may include other excipients such as plasticizers, tackifiers, sweeteners, flavors and the like to modify the adhesives sensory and rheological characteristics.

Many derivatives of a lower alkyl vinyl ether and maleic anhydride copolymer or maleic acid copolymer other than the sodium and the calcium partial salts mentioned above have been disclosed as effective denture adhesive compositions. U.S. Pat. No. 4,521,551 to Chang et al. teaches and claims various denture fixative compositions comprising a water soluble partially neutralized alkyl vinyl ether maleic acid/anhydride copolymer and at least one hydrophilic polymer such as sodium carboxymethyl cellulose, polyethylene oxide or hydroxypropyl guar. When contacted with saliva, said composition develops a high degree of tack and viscous mucilage which readily spreads over the denture-mucosal interface so as to fill the gaps between the dentures and gum and provides a suction-type seal.

U.S. Pat. No. 5,006,571 to Kumar et al. describes a denture adhesive composition consisting of petrolatum, natural and synthetic oils, waxes, vegetable oil waxes and the like. The useful oils mentioned include mineral oil, vegetable oils such as corn, soy bean, cottonseed, castor, palm and coconut oils and animal oils such as fish oil and oleic acid. In general, the oils are incorporated in amounts of about 1.0% to about 30.0% by weight of the total denture adhesive composition with amounts of from about 20% to about 25% being preferred. An optional component in the formulation of the invention is the use of fumed silica in the amount of from about 0.5% to 6.0%.

U.S. Pat. No. 5,093,387 to Schobel et al. discloses a denture adhesive base composition with an anhydrous mixture of cationic derivatives of guar gum, a mixed sodium/calcium salt of methyl vinyl ether maleic anhydride and sodium carboxymethyl cellulose. Fumed silica is disclosed as an optional additive in the formulation of the adhesive. The paste base material also includes a selected group of natural and synthetic oils and mixtures thereof. At least one paste base material is selected from the group consisting of petrolatum, synthetic oils and mixtures thereof.

U.S. Pat. No. 4,758,630 to Shah et al. teaches an effective denture fixative composition comprised of the zinc or strontium partial salts of a lower alkyl vinyl ether and maleic acid copolymer wherein the zinc and strontium cations are "unmixed" with any other cations or ester functions in the copolymer salt. Also, U.S. Pat. No. 5,073,604 to Holeva et al. discloses zinc or strontium partial salts of a lower alkyl vinyl ether and maleic acid copolymer, wherein the zinc and strontium are "mixed" with calcium cations and optionally sodium cations in the copolymer salt. U.S. Pat. No. 5,304,616 to Rajaiah et al. further teaches mixed salts of sodium, iron, strontium and zinc cations of a lower alkyl vinyl ether and maleic acid copolymer as effective denture fixatives. And in a similar disclosure, U.S. Pat. No. 5,204,414 to Pelah et al., describes the use of a trivalent metal salt such as aluminum in combination with a calcium and/or sodium cation which when reacted with a lower alkyl vinyl ether and maleic acid copolymer forms an effective denture fixative composition.

U.S. Pat. No. 5,001,170 to Keegan discloses and claims a denture adhesive base composition comprised of a substantially anhydrous mixture of methyl vinyl ether-maleic acid copolymer, polyvinyl pyrrolidone and an ethylene oxide polymer. A denture adhesive compound of this base is also disclosed which optionally includes hydroxy-propyl methylcellulose. The composition allegedly provides superior adherent properties over prolonged periods of time and adverse conditions.

Finally, U.S. Pat. No. 5,304,616 to Rajaiah et al. discloses and claims novel denture stabilizing compositions that allegedly exhibit improved hold. The compositions consist of specific mixed partial salts of a lower alkyl vinyl ether-maleic acid copolymer wherein 15%–40% of the functional groups of the acid polymer exist as the free carboxylic acid and the remainder are substituted with 0.1% to 80% strontium cations and/or 0.1% to 65% zinc cations. These re-mixed partial salts are then combined with a water-sensitive polymeric material such as natural gums, synthetic polymers, polysaccharides and cellulose derivatives to form the stabilized adhesives.

However, in spite of the vast number of adhesive compositions developed by and existing in the prior art, many of which are commercially available in one form or another, consumer preference studies have indicated that hold performance of a denture adhesive is still the single most important attribute of the adhesive and many consumers feel there still exists room for improvement. The denture adhesive compositions of the present invention afford excellent adhesion of the dentures to the oral tissues of the gums and jaw regions of the mouth with excellent cohesive properties and a high degree of tack to prevent denture sliding. The composition possesses a soft, pasty texture with a very pleasant taste and mouthfeel.

SUMMARY OF THE INVENTION

The present invention is an improved denture adhesive comprising the mixed partial salt of a lower alkyl vinyl ether-maleic acid copolymer wherein at least one cation is zirconium and a second cation is selected from the group consisting of calcium, zinc, magnesium, strontium, iron and mixtures thereof. Optionally, a third cation such as sodium or potassium may also be present.

DETAILED DESCRIPTION OF THE INVENTION

Many of the presently commercially available dental adhesive paste consist of a dispersion of water sensitive mixed polymer particles in a hydrocarbon vehicle. The mixed partial zirconium salts of the lower alkyl vinyl ether-maleic acid copolymers of the present invention provide a denture adhesive base that can be formulated into a superior dental fixative as the salt particles enable the adhesive to absorb moisture more rapidly in the mouth than the prior art adhesives have been able to do. More rapid water absorption results in faster particle swelling, faster particle softening and a greater degree of coalescence. These characteristics and properties allow the composition to form a continuous adhesive gel that spreads uniformly throughout the dental plate for superior adhesion and performance. Generally the denture adhesive compositions of this invention will also include sodium carboxymethylcellulose which increases the rate of water absorption.

The lower alkyl vinyl ether maleic acid copolymer from which the mixed partial salts are derived is a polymer backbone of the following structural unit:

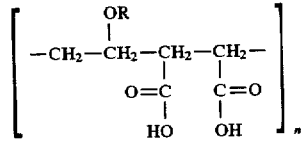

where R represents a $C_1$–$C_5$ alkyl radical, n is an integer greater than 1.0 and represents the number of repeat occurrences of this structural unit in a molecule of the copolymer. The number of structural units (n) in the copolymer molecule is also that which will give the compound a specific viscosity of more than 1.2 as determined in MEK at 25° C.

The mixed partial salt of the lower alkyl vinyl ether maleic acid copolymer is comprised of two or more cations, at least one being zirconium (Zr). The second cation is selected from the group consisting of calcium (Ca), zinc (Zn), magnesium (Mg), strontium (Sr) or iron (Fe). The mixed partial salt may be a dual salt, i.e. zirconium and calcium or zirconium and magnesium or, optionally, may include a third alkali metal salt i.e., sodium (Na) or potassium (K), etc., and thereby comprise a tripartite mixed partial salt such as the zirconium-calcium-sodium or the zirconium-magnesium-sodium salt of the lower alkyl vinyl ether maleic acid copolymer.

The mixed partial zirconium and calcium, magnesium, zinc etc., salts of the polymethyl vinyl ether maleic acid copolymer are prepared by the step-wise addition of the carbonates, oxides or hydroxides of the respective metal to the vinyl ether maleic acid copolymer in an aqueous solution at elevated temperatures with agitation. Preparation of the polymethyl vinyl ether-maleic anhydride copolymer is specifically set forth in U.S. Pat. No. 5,047,490 to Pelah et al. which is hereby incorporated by reference. The polymethyl vinyl ether maleic anhydride copolymer is also commercially available under the trade name GANTREZ® AN from ISP, Wayne, N.J.

Specifically, the polymethyl vinyl ether-maleic anhydride copolymer is first dissolved in water at elevated temperatures of from about 75° C. to about 100° C. and stirred until complete dissolution occurs. At this point the anhydride form of the polymer converts to the acid. Hydrous zirconium carbonate is added and stirred for a sufficient period of time to insure complete and uniform dispersion and reaction with the copolymer. Next a slurry of calcium hydroxide in water is added in a likewise fashion and agitation is continued. If the sodium tripartite salt is prepared, a solution of sodium hydroxide is added and heating and stirring are continued until the partial salts of the copolymer form which result in a viscous solution. The viscous solution is then poured into trays and dried under elevated temperatures to yield the solid partial zirconium, calcium and sodium copolymer salt product.

The mixed partial zirconium with magnesium and/or sodium salts can be made similarly with magnesium oxide, sodium hydroxide, etc. replacing calcium hydroxide. The copolymer salt is then formulated into an adhesive paste or powder using ingredients known in the art including sodium carboxymethylcellulose, waxes, oils, preservatives, flavoring agents, colorants, sweetening agents, viscosity modifiers and the like.

The waxes useful in the present invention comprise both natural and synthetic waxes and include, without limitation, animal waxes such as beeswax, lanolin and shellac wax, vegetable waxes such as carnauba, candelilla and bayberry waxes and mineral waxes such as petroleum including paraffin, and microcrystalline waxes.

The oils useful in the invention include without limitation mineral oil, vegetable oil such as corn, soybean, cottonseed, castor, palm and coconut oils and animal oil such as fish oil and oleic acid.

Flavoring agents well known to the denture adhesive art may be added to the compositions of the instant invention. These flavoring agents may be chosen from synthetic flavor oils and/or natural oils derived from plants, leaves, flowers, fruits and combinations thereof. Representative flavor oils include: spearmint oil, menthol, cinnamon oil, oil of wintergreen (methylsalicylate) and peppermint oils. Also useful are artificial, natural or synthetic fruit flavors such as citrus oil including lemon, organte, lime and grapefruit, and fruit essences including apple, strawberry, cherry, grape, pineapple and so forth. The flavoring agent may be liquid, spray dried, encapsulated, sorbed on a carrier and combinations thereof. A preferred flavoring agent is peppermint oil, commercially available from Rose Mitchum. The amount of flavoring agent utilized may vary depending on such factors as flavor type, adhesive formulation and strength desired. In general, amounts of about 0.01% to about 5.0% by weight of the total denture adhesive composition are usable, with amounts of about 0.05% to 0.15% being preferred.

Preservatives which may be used in the denture adhesive formations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl polycarbonate and phosphates. The parabens include the methyl, ethyl, propyl, and butyl esters of parahydroxybenzoic acid. Methyl paraben and propyl paraben are the preferred preservatives of the invention, preferably utilized in amounts of about 0.03% to about 0.6% by weight of the total denture adhesive composition.

The denture adhesive compositions may also include the use of sweeteners well known in the art.

The sweetening agent may be selected from a wide range of materials including water-soluble agents, water-soluble artificial sweeteners, and dipeptide-based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e. sodium or calcium saccharin salts, cyclamate salts, acesulfame-K, sucralose and the like, and the free acid form of saccharin.

C. Dipeptide-based sweeteners such as L-aspartyl-L-phenylalanine methyl ester and materials described in U.S. Pat. No. 3,491,131, L-D-aspartyl-N-(2,2,4,4-tetramethyl-3-thietanyl-D-alaninamide hydrate) and the like.

In general, the amount of sweetener will vary with the desired amount of sweetener selected for a particular denture adhesive formulation. This amount may be about 0.001% to about 5% by weight of the final denture adhesive composition when using an easily extractable sweetener.

The colorants useful in the present invention include the pigments such as titanium dioxide, and may also include dyes suitable for food, drug and cosmetic applications. These colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of the 4-[4-Methyl-p-sulfobenzylamino) diphenylmethylene]-[1-(N-ethyl-N-P-sulfobenzyl)-2 5-cyclohexadienimini]. A full recitation of F.D. & C. and D. & C. colorants and their corresponding chemical structures may be found in the Kirk-Othmer Encyclopedia of Chemical Technology, 3rd Edition, Volume 5, at pages 561–595.

The vehicle viscosity modifiers useful herein include polyethylene, its derivatives and petrolatum.

When a mineral oil vehicle is employed, polyethylene is used as a thickening agent to provide a "synthetic petrolatum" vehicle, and thus is used to adjust the extrusion (application) properties of the finished composition. Polyisobutylene may also be used in conjunction with polyethylene to further enhance the viscosity properties of the vehicle. Alternatively, a stock petrolatum, with or without mineral oil, may be employed depending upon the specific handling qualities which are desired in the final product.

The remaining aqueous phase viscosity modifiers useful in the present invention (sodium alginate, sodium carboxymethylcellulose, etc.) belong to the gum block of the denture adhesive. These agents have some impact on the extrusion qualities of the adhesive, but generally they are functionally dormant until they are activated by saliva in the mouth.

In a preferred aspect of the invention, the denture adhesive base composition may further include at least one paste base material selected from the group consisting of petrolatum, natural and synthetic oils and mixtures thereof.

The denture adhesive composition may be in the form of a paste, liquid, or powder mixture. The means for preparing such formulations is well known in the denture adhesive art.

The following examples are provided to better describe and set forth ways in which to prepare the denture adhesive compounds of the present invention. They are for illustration purposes only however, and it is recognized that minor changes and variations may be made to these compositions not contemplated herein. To the extent that any such changes do not materially affect the chemical make-up or functionality of the final product, such changes are considered to be within the spirit and scope of the invention as recited by the claims that follow.

EXAMPLE 1

A mixed partial zirconium, calcium and sodium salt of polymethyl vinyl ether maleic acid (GANTREZ® AN 169 acid) was prepared by adding GANTREZ® AN169 198 g. to 2800 ml. of vigorously mixed deionized (DI) water. The mixture was heated to 90° C. and held at this temperature during the remaining additions. When the copolymer solution became clear, it was maintained at 90° C. for one hour with continued mixing. Then a slurry of hydrous zirconium carbonate 14.1 g. in 350 ml of DI water was added to the polymethyl vinyl ether-maleic acid solution and the reaction mixture was mixed for 0.5 hour. A slurry of calcium hydroxide 42.3 g. in 300 ml. of DI water was added gradually to the acid solution and the reaction mixture was again mixed for another for 0.5 hr. Finally, a solution of sodium hydroxide, 15.2 g. in 300 ml. of DI water was added to the acid solution and the reaction mixture was mixed for 0.5 hour. The resulting solution is translucent with precipitation. While maintaining batch temperature and mixing speed, the solution of the partial salt is discharged into trays and dried in a 55° C. oven until testing indicated the salt was dry. The salt was milled and then used to make a denture adhesive paste formulation. The paste adhesive was evaluated in a subjective test for adhesive performance. The test results presented in Table I show this salt (salt No. 3) containing 10% zirconium tested superior to a prior art sodium and calcium salt prepared in Example 2.

EXAMPLE 2

A mixed partial sodium and calcium salt of polymethyl vinyl ether maleic acid of the prior art was prepared following the method of example 1. The raw materials employed are shown below:

| | |
|---|---|
| DI Water | 3750 ml. |
| Polymethyl vinyl ether-maleic anhydride (GANTREZ ® AN 169) | 216.8 g. |
| Calcium hydroxide | 24.0 g. |
| Sodium hydroxide | 11.1 g. |

The salt was evaluated by a subjective performance test after having been converted into adhesive paste as is known in the art. The comparative results are shown as salt No. 4 in Table I.

EXAMPLE 3

Two partial zirconium polymethyl vinyl ether maleic acid salts were prepared by the method of Example 1 except that only hydrous zirconium carbonate (no calcium hydroxide and sodium hydroxide) was used.

| | Salt #1 | Salt #2 |
|---|---|---|
| DI water | 3750 ml. | 3750 ml. |
| GANTREZ ® AN 169 | 280.2 g. | 260.4 g. |
| Hydrous Zirconium Carbonate | 29.8 g. | 39.6 g. |

A translucent salt solution was obtained when completed. These salts, after conversion into paste adhesive, were also evaluated by the subjective performance test as shown in Table I (salts 1 and 2).

EXAMPLE 4

A mixed partial zirconium, calcium and sodium salt of polymethyl vinyl ether maleic acid was prepared following the method of Example 1. The raw materials employed are shown below:

| | |
|---|---|
| DI water | 3750 ml. |
| Polymethyl vinyl ether maleic anhydride (GANTREZ ® AN 169) | 208.5 g. |
| Calcium Hydroxide | 44.7 g. |
| Hydrous Zirconium Carbonate | 14.7 g. |
| Sodium Hydroxide | 32.1 g. |

The resulting salt solution was clear. After drying the solution, the salt was milled, and then employed in the preparation of the same denture adhesive paste formula used in the previous examples. The paste adhesive was evaluated in the subjective test for adhesive performance. The test results presented in Table I show the formulation containing the additional 10% zirconium (salt No. 5) tested superior to a prior art sodium and calcium salt described in Example 2.

TABLE I

Subjective Test Results for Experimental Paste Adhesives Containing Partial Gantrez Salts

| | Metal Ion Degree of Substition Gantrez Salt Active based on Method of Synthesis | | | | Subjective Test Results | | |
|---|---|---|---|---|---|---|---|
| Salt # | % Zirconium | % Calcium | % Sodium | Salt Solution Appearance | on Paste Adhesive | | |
| | | | | | Hydration | Adhesion | Cohesion |
| 1 | 10 | — | — | Translucent | — | Fair | Poor |
| 2 | 20 | — | — | Translucent | — | Fair | Poor |
| 3 | 10 | 45 | 45 | Translucent with Precipitation | Good | Good | V. Good |

TABLE I-continued

Subjective Test Results for Experimental Paste Adhesives Containing Partial Gantrez Salts

| Salt # | Metal Ion Degree of Substition Gantrez Salt Active based on Method of Synthesis | | | Salt Solution Appearance | Subjective Test Results on Paste Adhesive | | |
|---|---|---|---|---|---|---|---|
| | % Zirconium | % Calcium | % Sodium | | Hydration | Adhesion | Cohesion |
| 4 | — | 70 | 10 | Translucent with Precipitation | Good | Fair | Fair |
| 5 | 10 | 45 | 30 | Clear | Good | V. Good | Good |

What we claim is:

1. A mixed partial salt of a lower alkyl vinyl ether maleic acid copolymer comprising the repeating structural unit:

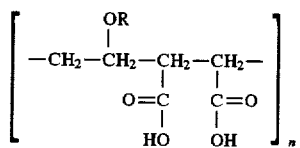

where R represents a $C_1-C_5$ alkyl radical and n is an integer greater than 1.0 representing the number of repeat occurrences of this structural unit in a molecule of this copolymer and wherein n is a value such that the specific viscosity of this copolymer is greater than 1.2, the specific viscosity being measured in MEK (methyl ethyl ketone) at 25° C., said partial salts containing at least one cation consisting of zirconium and a second cation selected from the group consisting of calcium, magnesium, zinc, strontium, iron and mixtures thereof.

2. The mixed partial salt of claim 1 wherein R is methyl.

3. The mixed partial salt of claim 2 further comprising a third cation selected from the group consisting of sodium, potassium, lithium and mixtures thereof.

4. The mixed partial salt of claim 3 wherein said third cation is sodium.

5. An improved denture adhesive comprising the mixed partial salts of claims 1, 3 or 4.

6. The improved denture adhesive of claim 5 further comprising at least one additive selected from the group consisting of sodium carboxymethylcellulose, waxes, oils, preservatives, flavoring agents, viscosity modifiers, sweeteners, colorants and mixtures thereof.

7. The improved denture adhesive of claim 5 formulated as a paste, powder, or liquid.

8. An improved denture adhesive comprising an effective amount of a mixed partial salt of a polyalkyl vinyl ether maleic acid wherein at least 1 of said cations is zirconium and a second cation is selected from the group consisting of calcium, magnesium, strontium, iron, zinc and mixtures thereof.

9. The mixed partial salt of claim 8 further comprising a third cation selected from the group consisting of sodium, potassium, lithium and mixtures thereof.

10. The mixed partial salt of claim 9 wherein said third cation is sodium.

11. The improved denture adhesive of claim 10 further comprising at least one additive selected from the group consisting of sodium carboxymethylcellulose, waxes, oils, preservatives, flavoring agents, viscosity modifiers, sweeteners, colorants and mixtures thereof.

12. The improved denture adhesive of claim 11 formulated as a paste, powder, or liquid.

13. A method for securing dentures and other dental protheses to the gums of the oral cavity using the adhesive of claims 7 or 12.

* * * * *